(12) United States Patent
Elabbadi et al.

(10) Patent No.: US 8,808,771 B2
(45) Date of Patent: *Aug. 19, 2014

(54) ACTIVE INGREDIENT DELIVERY SYSTEM WITH AN AMORPHOUS METAL SALT AS CARRIER

(71) Applicant: Firmenich SA, Geneva (CH)

(72) Inventors: Amal Elabbadi, Annemasse (FR); Lahoussine Ouali, Vetraz-Monthoux (FR)

(73) Assignee: Firmenich SA, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/743,874

(22) Filed: Jan. 17, 2013

(65) Prior Publication Data

US 2013/0195929 A1  Aug. 1, 2013

Related U.S. Application Data

(63) Continuation of application No. 12/517,338, filed as application No. PCT/IB2007/054975 on Dec. 7, 2007, now Pat. No. 8,383,175.

(30) Foreign Application Priority Data

Dec. 12, 2006  (EP) .................................... 06125857

(51) Int. Cl.
*A23D 7/005* (2006.01)
*A23L 1/30* (2006.01)
*A61K 9/16* (2006.01)
*A61K 47/48* (2006.01)
*A23L 1/304* (2006.01)
*A61K 47/02* (2006.01)

(52) U.S. Cl.
CPC ......... *A61K 47/48792* (2013.01); *A23L 1/3006* (2013.01); *A23V 2002/00* (2013.01); *A61K 9/1611* (2013.01); *A23L 1/3008* (2013.01); *A23L 1/304* (2013.01); *A61K 47/02* (2013.01)
USPC .................. 426/98; 426/74; 426/89; 426/267

(58) Field of Classification Search
CPC ..................................... A23L 1/3006
USPC ........................ 426/98, 267, 74, 89
See application file for complete search history.

(56) References Cited

U.S. PATENT DOCUMENTS 8,383,175 B2 *  2/2013  Elabbadi et al. ................ 426/98

\* cited by examiner

*Primary Examiner* — Lien T Tran

(57) ABSTRACT

An active ingredient delivery system and a method of making or using the same, wherein the delivery system includes an active ingredient and a carrier component of an amorphous metal salt, with the active ingredient at least partly fixed to and partly encapsulated by the carrier component. The active ingredient may be a bitter tasting polyphenol such as a flavonoid.

9 Claims, No Drawings

ACTIVE INGREDIENT DELIVERY SYSTEM WITH AN AMORPHOUS METAL SALT AS CARRIER

This application is a continuation of application Ser. No. 12/517,338 filed on Jun. 2, 2009, now U.S. Pat. No. 8,383,175.

TECHNICAL FIELD

The present invention relates to a delivery system for active ingredients, a method of preparing the delivery system and the use of the delivery system to mask bitter tastes.

BACKGROUND AND PRIOR ART

It is well known that certain consumable products in the foods, beverages and drugs industries contain bitter substances that are detrimental to the overall flavour impact of the product being consumed. In order to deal with this, manufacturers have gone to great lengths to mask or even remove the offending products.

The problem is particularly acute in beverages such as beer, coffee, and soft drinks where it is believed that the presence of polyphenols, such as chlorogenic acid lactones or flavonoids, contribute significantly to bitterness perception by consumers.

Nevertheless, many polyphenols or flavonoids found in foodstuffs are beneficial anti-oxidants which, when consumed, scavenge so-called "free radicals" or modulate human or animal gene expression and so provide nutritional or health benefits to the consumer. For a more detailed understanding of the beneficial effects of flavonoids, for instance, see "Flavonoids: A review of probable mechanisms of action and potential applications", Nijveldt et al, Am J Clin Nutr 2001; 74:418-25.

Therefore, it would be desirable to mask or otherwise inhibit the undesirable flavours imparted by such ingredients without detrimentally affecting their beneficial effect.

It is also known to extract these beneficial ingredients from foodstuffs so as to provide them in an isolated form, such as a nutritional supplement, which can be consumed in order to receive the benefit directly. However, in this concentrated form, the risk of consumer rejection due to the bitterness of the product is even more acute.

For such products, it would also be desirable to provide them in a more palatable format with the perception of unpleasant bitterness significantly reduced or even removed entirely.

A further problem with such active ingredients is that they are highly sensitive to oxidation. Therefore, it would also be desirable to provide a system that is capable of protecting the active ingredients against such degradation.

JP 2003-128664 describes neutralizing polyphenols to the corresponding sodium, calcium, magnesium or potassium salt in order to reduce of bitterness. This method forms large particles that change dramatically the appearance of drinks (such as tea) and even generates undesirable sediment.

In JP 2003-366456 (Taiyo Kagaku KK) the bitterness and astringency in beverages and foods is said to be decreased by the addition of casein.

In JP 04-103771 (Unitika KK), a tea extract is prepared by blending tea with chitin so as to eliminate bitterness and astringency.

US-A1-2002/0188019 (Bayer Corporation) describes preparations comprising certain hydroxyflavanones which are said to mask bitter or metallic taste sensations.

U.S. Pat. No. 5,741,505 (Mars) describes using inorganic coatings to provide an oxygen barrier to increase the shelf-life of foods and pharmaceutical products. The coating does not interact with the encapsulated product.

US 2004/0180097 (Lin et al) refers to a stable and/or taste-masked pharmaceutical dosage form comprising porous apatite grains and a drug entrapped in the pores. The product is formed by contacting blank porous apatite grains, typically in the form of slurry, with a solution of the drug and evaporating the solvent of the solution in order to entrap the drug in the porous apatite grains. Thus, there will be a high concentration of the drug at or near the surface of the granules with little or no complexation between the granules and the entrapped drug.

Finally, there are numerous products available to the public in which a liquid active ingredient, such as garlic oil, is encapsulated in a transparent shell. These capsules are very large, typically having a diameter of up to 5 to 10 mm.

It would also be desirable to provide particles having a diameter that is, at most, barely noticeable with the naked eye. Such particles are then suitable for incorporation into products, especially beverages, where the presence of visible particles is undesirable. For instance, tea is usually presented as a transparent drink (prior to the optional addition of milk) and the presence of visible particles therein would be deleterious to consumer appeal.

Various studies have also shown that the beneficial effects on health due to, for instance polyphenols, can be increased by the delivery of the intact active to the digestive system.

Thus, it would be desirable to protect the active ingredient in such a way that release is triggered by physical conditions present in the stomach or digestive system but which are not present during conventional storage or in the oral cavity.

The present invention seeks to address one or more of the abovementioned problems and/or to provide one or more of the abovementioned benefits.

SUMMARY OF THE INVENTION

Accordingly, the present invention provides an active ingredient delivery system, the system comprising
 (i) an active ingredient and
 (ii) a carrier component,
wherein the carrier component comprises an amorphous metal salt and the active ingredient is at least partly fixed to and partly encapsulated by the carrier component.

The invention also provides a method of preparing an active ingredient delivery system comprising the steps of:
 (i) providing a first source of metal ions,
 (ii) providing a second separate source of anionic counterions,
 (iii) providing a third separate source of an active ingredient,
 (iv) combining the three sources in a mixing zone, and
 (v) performing a mixing step in the mixing zone,
so as to partly fix and partly encapsulate the active ingredient in a carrier component.

In another aspect, the invention provides the use of a carrier material, as defined above, to mask, inhibit or otherwise reduce a consumer's perception of bitterness due to the active ingredients defined above.

In yet another aspect the invention provides a food or beverage product comprising the delivery system defined above.

In still another aspect, the invention provides a nutritional, nutraceutical or pharmaceutical product comprising the delivery system defined above.

DETAILED DESCRIPTION OF THE INVENTION

The present invention relates to a delivery system product comprising a carrier component which comprises an amorphous metallic salt. Without wishing to be bound by theory, it is believed that the metallic salt acts as a hybrid fixing-encapsulating agent so that an active ingredient partly reacts with and partly is embedded therein.

As will be readily understood by the person skilled in the art of encapsulation, the hybrid carrier component is entirely different from conventional encapsulation products since the latter usually comprise either an encapsulating shell which fully surrounds the active ingredient (the so-called "core-shell" arrangement) or a matrix throughout which the encapsulated product is distributed (see, for example, U.S. Pat. No. 3,704,137).

It has been found that this hybrid carrier component also enables release of the active ingredient either by mechanical defragmentation in the digestive tract and/or by pH changes in the stomach and so provides a useful mechanism for delivering active ingredients, such as nutritional or health products, intact to where they are most effective.

The active ingredient delivery system may be in the form of a colloidal hybrid.

It has been found that such colloidal hybrids have a large specific surface area. This is advantageous because, when the conditions are suitable for releasing the encapsulated ingredient (e.g. due to the acidic pH in the stomach), there is more reactive surface area available which accelerates the rupture/dissolution of the carrier component and so enables release of the active ingredient to occur more rapidly at the desired location.

Carrier Component

The carrier component comprises an amorphous metal salt.

When referring to the amorphous metal salt, the phrase "carrier component" is used herein for the sake of brevity and denotes a material which is capable of both fixing and encapsulating an active material.

By "fixing", it is meant that the carrier preferably forms a bond, such as a complex, with the active ingredient. Of course, other types of bond may be envisaged by the person skilled in the art, though complexing is preferred.

By "encapsulating", it is meant that the carrier component forms, at least partly, a protective layer or shell around the active ingredient.

It is believed that by both fixing and encapsulating the active ingredient, the ingredient is homogeneously distributed throughout the carrier, unlike the heterogeneous distribution that would be expected where the carrier is porous and the active ingredient is simply entrapped in the pores. In the latter instance, the active ingredient would be expected to be concentrated at or near the surface of the carrier.

The metal salt has an amorphous structure. "Amorphous", as defined herein, is used to mean at least partly non-crystalline (i.e., a significant part of the compound lacks a distinct crystalline structure).

Thus, it should be understood that the amorphous metallic salts used as the hybrid carrier component might contain amounts of microcrystalline matter that can be tolerated without meaningful effect on the gross physical characteristics of these materials or on the enhanced complexation-encapsulation benefits that they provide.

In the context of the present invention, a metallic salt is amorphous if it contains less than about 50%, preferably less than about 40%, more preferably less than about 30%, even more preferably less than 10%, most preferably less than 5%, e.g. less than 2% by weight of crystalline material, based on the total weight of the inorganic salt.

The metallic salt is preferably substantially water-insoluble. "Substantially water-insoluble" is defined herein as meaning a solubility of less than $10^{-3}$ g/cc, more preferably less than $10^{-4}$ g/cc and most preferably less than $10^{-5}$ g/cc, when measured at 20° C. and at a pH between 3 and 7.

Thus, the metallic salt is preferably in the form of a solid at the pH typically encountered during storage.

Preferably, the metallic salt is soluble at acidic pH. More preferably, the inorganic salt has a solubility of greater than $10^{-3}$ g/cc, more preferably greater than $10^{-2}$ g/cc and most preferably greater than $10^{-1}$ g/cc, when measured at 37° C. and pH 2 or lower.

In other words, the pH typically found inside the stomach of a consumer will cause the rupture/dissolution of the carrier component and the eventual release of the active ingredient encapsulated therein.

Examples of metal cations suitable for use in the hybrid carrier component include calcium, magnesium, iron (II), iron (III), zinc or mixtures thereof.

More preferably, the metal cation is either calcium (II), magnesium (II) or a mixture thereof. Most preferably, it is calcium (II).

Examples of anionic counterions suitable for use in the hybrid carrier component include phosphates and carbonates.

The preferred counterion is phosphate because this has been found to generate an amorphous metallic salt having hydrophobic splitting planes which facilitate binding of the salt to the material being encapsulated.

Amorphous calcium phosphate (herein referred to as "ACAP") is the most preferred metallic salt. It is a water-insoluble and acid-soluble salt, particles of which can be prepared at neutral pH with high colloidal stability. This gives the benefits of a colloidal hybrid, as discussed above.

ACAP precipitates both with the inclusion of hydroxyl ions as well as with protons in the structure, depending on pH conditions, the neutral point typically being at pH 4.5. Thus under standard conditions at about pH 7, an amorphous metallic cross, typically being hydroxyapatite, is precipitated.

ACAP can also be calcium ion rich or phosphate ion rich, depending on the relative reactant streams entering the mixing zone.

A majority of the charge mismatch is then counterbalanced by hydroxyl groups or protons, respectively. This insensitivity against stoichiometry gives an enormous structural freedom to ACAP, allowing particle size, refractive index, amount of residual water in the precipitate, as well as mechanical plasticity to be controlled.

The molar ratio of calcium ions to phosphate ions is preferably from 3:1 to 1:3, more preferably from 2:1 to 1:3, even more preferably from 1:1 to 1:3, most preferably from 1:1.5 to 1:3.

It is preferred that the carrier comprises an excess of the anion since the resulting negatively charged carrier has a greater colloidal stability and/or is more easily dispersed in aqueous liquid formulations, such as tea, coffee, soft drinks and cordials.

A carrier component comprising an amorphous inorganic salt for use can be prepared in any suitable manner known to the person skilled in the art. Typically, it is prepared in situ at the same time as binding and encapsulating the active ingredient. For instance, the delivery system can be prepared by precipitation of inorganic salts in the presence of a liquid solution containing the active ingredient (e.g. a polyphenol).

For water insoluble actives, the delivery system can be prepared by co-precipitation of inorganic salts and active ingredient. The precipitation is typically carried out by introducing separate sources of the metal cation, anionic counterion and active material to be encapsulated into a mixing zone and causing a precipitation-encapsulation process to occur in this zone.

Additional materials may be present together with the amorphous metallic salt to make a complex carrier material. Organic materials are particularly preferred. For instance, carbohydrates such as maltodextrin, cyclodextrins and chemically modified starches may also be present so as to form a complex carrier material.

Active Ingredient

The active ingredient can be any compound or composition that it is desirable to fix and to encapsulate.

Nevertheless, the present invention has been shown to work surprisingly well at masking undesirable flavours whilst allowing them to be delivered intact for release in the digestive tract or stomach of a consumer.

In particular, the hybrid carrier component has been shown to mask bitter or astringent tastes particularly effectively.

It has also been shown to prevent undesirable oxidation of active ingredients which are particularly susceptible to oxidative degradation.

Preferred active ingredients include polyphenols, conjugated polyphenols, polyphenol polymers, coumarins, polysaccharides, lipids, organosulphur compounds, conjugated vitamins, peptides, carotenoids, proteins or mixtures thereof.

In one aspect, the active material is a preferably a polyphenol.

A particularly preferred polyphenol is a glycone optionally conjugated with one or more of methyl groups, sulphates, glycosides, phosphates, acetates and esters.

Examples of suitable polyphenols include the family of flavonoids.

Flavonoids include (i) flavones, such as chrysin, kaempferol, rutin, quercetin, luteolin and apigenin, (ii) flavanols, such as quercetin, kaempferol, myricetin, isorhamnetin, pachypodol, rhamnazin, (iii) flavanones, such as fisetin, naringin, naringenin, hesperetin, naringenin, eriodictyol, (iv) flavan-3-ols such as (+)-Catechin, (+)-Gallocatechin, (−)-Epicatechin, (−)-*Epigallocatechin, (−)-Epicatechin 3-gallate, (−)-Epigallocatechin 3-gallate, theaflavin, theaflavin-3-gallate, theaflavin 3'-gallate, theaflavin 3,3' digallate, (v) thearubigins, (vi) isoflavones such as genistein, daidzein, glycitein, (vii) anthocyanidins such as cyanidin, delphinidin, malvidin, pelargonidin, peonidin and petunidin, (viii) polymethoxyflavones, (ix) flavans, (x) phenolic flavanoids, (xi) proanthocyanidins and (xii) isoflavonoids.

Polyphenol active ingredients are found in a variety of natural consumer products such as grapefruit juice, green tea, black tea, and coffee as described by Adam Drewnowski and Carmen Gomez-Cameros 2000, *The American Journal of Clinical Nutrition*. The carrier component is particularly effective when used in combination with such foodstuffs or their extract. For instance, active ingredients comprising green tea extract or fermented tea extract are particularly suitable.

In another aspect, the active ingredient may be a colorant, more preferably a carotenoid. Examples of suitable carotenoids include beta-carotene, retinol, astaxanthin, lutein, lycopene, cryptoxanthin and zeaxanthin. Colorants such as this are typically used in translucent beverages. Upon storage, the colorant can sometimes settle to give an undesirable difference in colour shades throughout the beverage. Furthermore, vigorous shaking is then needed to redisperse the colorant evenly throughout the beverage. Using the hybrid agent to complex-encapsulate the colorant, the very small encapsulated particles then remain evenly suspended throughout the beverage, even upon storage.

Other suitable active ingredients include phenolic acids, tocopherol phosphates, tocopherol acetates, stilbenes, resveratrols, curcumins, vitamins, 6-gingerols, furanocoumarins, bergamottins, triterpens (limonoids), tannins, punicalagins, punicocides, ellagic acids, lignans, procyanidins, pycnogenols, phytosterols, glucosynolates, hydrolyzed glucosinolates, isothiocyanates, sulphoraphanes, glutathiones, ergothioneines, lipoic acids, sphingolipids and butyrates.

The active ingredient may be an oil.

A preferred oil which can be encapsulated in the present active ingredient delivery system is, for instance, an oil rich in polyunsaturated fatty acids. Such oils typically comprise at least 5 wt. %, preferably at least 10 wt. %, more preferably at least 25 wt. %, and most preferably at least 35 wt. % polyunsaturated fatty acids based on the total weight of the oil.

The oil rich in polyunsaturated fatty acids is preferably an oil rich in omega-3 fatty acids.

More preferably, the polyunsaturated fatty acids are selected from eicosapentaenoic acid (EPA), docosahexaenoic acid (DHA), arachidonic acid (ARA), α-linolenic acid, linoleic acid, and a mixture of at least two thereof. DHA and EPA are most preferred.

It is preferred that the oil is mixed with a vegetable oil derivative, such as a triglyceride oil. A particularly preferred range of commercially available oils are sold under the name Neobee® (ex Stepan).

A preferred weight ratio of oil rich in polyunsaturated fatty acids to vegetable oil derivative is from 70:30 to 99:1, more preferably from 80:20 to 95:5.

In a highly preferred embodiment, the oil mixture is then emulsified using any suitable emulsifying agent. Preferably the emulsifier is food grade, more preferably it is a sugar ester. The emulsified oil is found to mix more readily with the carrier system and so provides a more stable product.

Due to its hybrid nature, the delivery system of the present invention allows for very heavy loading of the active ingredient onto and into the carrier component whilst, surprisingly retaining a high degree of bitterness masking, as perceived by the consumer.

Thus, the active component may comprise up to 70% by weight of the total weight of the delivery system, more preferably from 10 to 65% by weight, most preferably from 20 to 55% by weight.

The advantage is that less carrier component is need in order to deliver the required amount of active ingredient thereby increasing cost effectiveness when compared to traditional encapsulation systems.

Delivery System Structure

The delivery system may be in solid, semi-solid or liquid form.

If solid, it is preferably in the form of particles.

The delivery system particle size is preferably from 10 to 1000 μm, more preferably from 20 to 500 μm, most preferably from 50 to 300 μm.

In the context of the present invention, "particle size" is defined as the arithmetic mean diameter determined by conventional light scattering experiments.

The particle size is particularly important insofar as it determines whether the particle can be used in food or beverage products where visibility of such particles is undesirable. It has been found that the delivery system according to the invention enables the preparation of much smaller particles than typically possible with conventional encapsulated products.

Preferably at least 90%, more preferably at least 95% and most preferably 97%, e.g. 99% by number of the particles have a particle size within the range of from 10 to 1000 μm, more preferably from 20 to 500 μm and most preferably from 50 to 300 μm.

It has been discovered that the particles in the delivery system of the present invention typically have a much more homogeneous size than those in traditional encapsulation systems. Homogeneously sized particles are desirable from an aesthetic viewpoint and also allow for a more regular dosage of the active ingredient.

If the delivery system is in liquid form, it is preferably provided as an aqueous dispersion.

The active ingredient delivery system may be further encapsulated. A further encapsulation of the active ingredient delivery system is highly desirable since it enhances the oxidative stability of the delivery system upon storage.

A first preferred encapsulating system is a glassy matrix within which the active ingredient delivery system is held. More preferably the encapsulation system is a glassy carbohydrate matrix. The carbohydrate matrix ingredient preferably comprises a sugar derivative, more preferably maltodextrin.

Particularly preferred maltodextrins are those with a DE of from 10 to 30, more preferably from 15 to 25, most preferably from 17 to 19.

Typically, the active ingredient delivery system is admixed with a carbohydrate matrix material and an appropriate amount of a plasticizer, such as water, the mixture is heated within a screw extruder to a temperature above the glass transition temperature of the matrix material so as to form a molten mass capable of being extruded through a die and then the molten mass is extruded using established processes, such as described in the prior art. See, for instance, patent application WO 00/25606, published May 11, 2002 or WO 01/17372, published Mar. 15, 2001, and the documents cited therein, the contents of which are hereby included by reference.

If desired, further carbohydrate matrix components may be present to improve yet further the antioxidant barrier properties.

Other suitable encapsulation systems are described in, for examples, U.S. Pat. Nos. 4,610,890 or 4,707,367, the contents of which are included by reference.

Preparation

Typically the preparation of the active ingredient delivery system involves mixing together separately provided sources of (i) the metal ions, (ii) anionic counterions and (iii) source of active ingredient.

Nevertheless, it has been found possible to combine sources (i) and (iii). For instance, where the active ingredient is present in the form of an aqueous solution a water/organic solvent solution, a dispersion or an oil in water emulsion, sources (i) and (iii) can be combined using emulsifiers, preferably food-grade emulsifiers.

EXAMPLES

The invention will now be described with reference to the following examples. It is to be understood that the examples are illustrative of the invention and that the scope of the invention is not limited thereto.

Samples according to the invention are denoted by a number and comparative examples by a letter. All amounts are % by weight unless otherwise indicated.

Example 1

Encapsulation of Naringin with ACAP

A conventional double jet precipitation process, which can be operated both batch wise and in a continuous mode, was used. The active ingredient (Naringin) was firstly dissolved in ethanol or ethanol/water medium. A first stream comprising $Ca^{2+}$ ions (provided as calcium chloride solution) and a second stream comprising $PO_4^{3-}$ ions (provided as sodium phosphate), were prepared in order to give a resulting carrier component comprising ACAP solution at 10 g/L. A third stream comprising a standard solution of 2 g/L of naringin in 30% ethanol solution was then prepared.

The three streams were jetted separately into a mixing chamber using a standard y-mixer with the reaction being stopped for equal volumes, i.e. 10 ml $Ca^{2+}$ stock solution plus 10 ml $PO_4^{3-}$ stock solution into 10 ml naringin. The extinction coefficient (strong phenol band at 280 nm, slightly acidic conditions) was determined after standardized dilution with 30 wt % ethanolic solution (1:12) and was compared before and after the addition of the ACAP.

The results show that the E-value was lowered from 3.75 to 1.5 and, from this, it was calculated that at least 70% of the naringin was entrapped by the ACAP.

Example 2

Evaluation of Natural Consumer Products

The following samples were prepared:

TABLE 1

| Sample | Composition |
| --- | --- |
| A | Green tea |
| 1 | Green tea + ACAP |
| B | Black tea |
| 2 | Black tea + ACAP |
| C | grapefruit juice |
| 3 | grapefruit juice + ACAP |

Samples A, B and C were prepared as follows: The stirred Y-mixer was used to generate ACAP with 10 g/L base concentration, as in example 1. This in-situ generated colloid was jetted into three different natural polyphenol-containing solutions, i.e. 10 minute overbrewed black tea, 10 minute overbrewed green tea, and grapefruit juice. Final amount of addition were 100 mg raw starting products (corresponding to about 50 mg ACAP) per 100 ml of polyphenol-containing fluid, i.e. addition was in the 0.1% range.

Evaluation of the bitterness perceived was then carried out as follows:

A trained panel of 7 people were told to compare sample A and sample 1 and respond to the question "which of the pair of samples is more bitter?". This was then repeated for samples B and 2.

The results are given in the following table:

TABLE 2

| Sample | Results |
|--------|---------|
| A and 1 | 6 people rated sample A as more bitter |
| B and 2 | 6 people rated sample B as more bitter |
| C and 3 | 4 people rated sample C as more bitter |

This demonstrates that the delivery system provides significant bitterness masking benefits.

Example 3

Encapsulation of Fish Oil

A fish oil (tuna oil) sample was degasified by flowing nitrogen through it for a period of 1 hour. The degasified fish oil was then mixed with a medium chain triglyceride oil (Neobee, ex Stepan) and emulsified together with a sugar ester (Ryoto S-1670, ex Mitsubishi) using an Ultra-Turrax® homogenizer at 24000 rpm. Calcium and phosphate ion solutions were prepared in a 3-morpholinopropanesulfonic acid buffer (MOPS), to give a pH of 7.2. Arabic gum was added to the calcium solution in order to avoid the crystallisation of the calcium phosphate particles.

A double jet precipitation process was used to entrap the fish oil in the inorganic hybrid matrix. A first stream comprising 2% of $Ca^{2+}$ ions (provided as calcium chloride solution) and 0.2% of Arabic gum and a second stream comprising 2% of $PO_4^{3-}$ ions (provided as sodium phosphate), were prepared in order to give a resulting carrier component comprising ACAP solution at 10 g/L. A third stream comprising an emulsion of 25% of fish oil/Neobee (at a weight ratio of 90:10) was then prepared as indicated above. The concentration of Ryoto sugar ester S-1670 in the emulsion was 0.3%. The three streams were jetted separately into a mixing chamber using a standard y-mixer with the reaction being stopped for equal volumes. The resulting sample was concentrated by removing the water phase. The final sample was homogeneous and was found to have a fish oil content of 26%.

What is claimed is:

1. An active ingredient delivery system, the system comprising
   (i) an active ingredient, and
   (ii) a carrier component,
wherein the carrier component comprises an amorphous metal salt and the active ingredient is at least partly fixed to and partly encapsulated by the carrier component, wherein the active ingredient is an emulsified oil rich in polyunsaturated fatty acids.

2. The delivery system of claim 1, wherein the metal ion counterpart of the metal salt is selected from calcium, magnesium, iron (II), iron (III), zinc, or mixtures thereof.

3. The delivery system of claim 1, wherein the carrier component comprises an amorphous calcium phosphate salt.

4. The delivery system of claim 1, wherein the metal ions and anionic counterions in the metal salt are present at a molar ratio of 3:1 to 1:3.

5. The delivery system according to claim 1, wherein the system is further encapsulated.

6. A method of preparing the active ingredient delivery system of claim 1, comprising the steps of:
   (i) providing a first source of metal ions,
   (ii) providing a second separate source of anionic counterions,
   (iii) providing a third separate source of an active ingredient,
   (iv) combining the three sources in a mixing zone, and
   (v) performing a mixing step in the mixing zone so as to partly fix and partly encapsulate the active ingredient in a carrier component.

7. A method of masking, inhibiting or otherwise reducing bitterness perceived by a consumer of an active ingredient which comprises providing the active ingredient in the delivery system of claim 1.

8. A nutritional, nutraceutical or pharmaceutical product comprising the delivery system as claimed in claim 1.

9. A food or beverage product comprising the delivery system of claim 1.

* * * * *